(12) United States Patent
Speller et al.

(10) Patent No.: US 7,664,227 B2
(45) Date of Patent: Feb. 16, 2010

(54) INTELLIGENT ADAPTIVE X-RAY IMAGING SYSTEM

(75) Inventors: Robert Speller, Croddington (GB); Gary Royle, London (GB)

(73) Assignee: UCL Business PLC, London (GB)

( * ) Notice: Subject to any disclaimer, the term of this patent is extended or adjusted under 35 U.S.C. 154(b) by 187 days.

(21) Appl. No.: 11/801,782

(22) Filed: May 11, 2007

(65) Prior Publication Data
US 2008/0232550 A1   Sep. 25, 2008

Related U.S. Application Data

(60) Provisional application No. 60/808,135, filed on May 25, 2006.

(51) Int. Cl.
*A61B 6/00* (2006.01)

(52) U.S. Cl. ..................... 378/95; 378/98.12

(58) Field of Classification Search ............... 378/95, 378/98.7, 98.12, 207
See application file for complete search history.

(56) References Cited

U.S. PATENT DOCUMENTS

| | | | |
|---|---|---|---|
| 4,794,630 A * | 12/1988 | Ploix | 378/98.12 |
| 5,164,976 A * | 11/1992 | Scheid et al. | 378/146 |
| 5,506,877 A * | 4/1996 | Niklason et al. | 378/37 |
| 2006/0062353 A1* | 3/2006 | Yatsenko et al. | 378/156 |

OTHER PUBLICATIONS

Aslund, M. et al., "AEC for scanning digital mammography based on variation of scan velocity," Med. Phys. 32 (11), (Nov. 2005) pp. 3367-3374.
Cooney, P. et al., "Automatic Exposure Control in Fluoroscopic Imaging," Radiation Protection Dosimetry 57 (1995) pp. 269-272 (Abstract).
Denyer, P.B. et al., "CMOS Image Sensors for Multimedia Applications," IEEE 1993 Custom Integrated Circuits Conference (1993) pp. 11.5.1-11.5.4.
El Gamal, A. et al., "CMOS Image Sensors," IEEE Circuits and Devices Magazine 21 (3), (May/Jun. 2005) pp. 6-20.
Elbakri, I.A. et al., "Automatic exposure control for a slot scanning full field digital mammography system," Med. Phys. 32 (9), (Sep. 2005) pp. 2763-2770.

(Continued)

*Primary Examiner*—Chih-Cheng G Kao
(74) *Attorney, Agent, or Firm*—Blakely, Sokoloff, Taylor & Zafman (57) ABSTRACT

A method and an arrangement for an intelligent adaptive x-ray imaging system, in which the exposure conditions of the object to x-rays is dynamically controlled and optimized in real-time in order to provide the optimum diagnostic information. The arrangement splits the imaging beam into two separate fan beams that scan over the object in a single pass, where the first beam (scout) collects information from the object, that is analyzed to control the intensity or spectral quality or spatial distribution of the second beam (I-ImaS). The CMOS image sensors deployed in the arrangement are able to process detected information either on-chip or within a field programmable gate array, so as to compute a measure related to the diagnostic value of the information.

12 Claims, 5 Drawing Sheets

OTHER PUBLICATIONS

Eraso, F.E. et al., "Clinical and in vitro film quality comparison of manual and automatic exposure control in panoramic radiography," Oral Surg Oral Med Oral Pathol Oral Radiol Endod 87 (4), (Apr. 1999) pp. 518-523.

Mulkens, T.H. et al., "Use of an Automatic Exposure Control Mechanism for Dose Optimization in Multi-Detector Row CT Examinations: Clinical Evaluation," Radiology 237 (Oct. 2005) pp. 213-223).

Nixon, R.H. et al., "256 X 256 CMOS Active Pixel Sensor Camera-on-a-Chip," IEEE Journal of Solid-State Circuits, vol. 31, No. 12 (Dec. 1996) pp. 2046-2050.

Nyman, U. et al., "Patient-Circumference-Adapted Dose Regulation in Body Computed Tomography. A Practical and Flexible Formula," Acta Radiologica 46 (4), (2005) pp. 396-406.

Plewes, D.B. et al., "A scanning system for chest radiography with regional exposure control: Practical implementation," Med. Phys. 10 (5), (Sep./Oct. 1983) pp. 655-663.

Vlasbloem, H. et al., "AMBER: A Scanning Multiple-Beam Equalization System for Chest Radiography," Radiology 169 (Oct. 1988) pp. 29-34.

\* cited by examiner

INTELLIGENT ADAPTIVE X-RAY IMAGING SYSTEM

The present patent application is a non-provisional application claiming the priority of a provisional application, namely, U.S. Application No. 60/808,135, filed May 25, 2006.

TECHNICAL FIELD OF THE INVENTION

The present invention relates to an x-ray imaging system.

BACKGROUND OF THE INVENTION

Imaging systems able to control the X-ray source output are known to exist, in particular the use of automatic exposure control (AEC) is available on many systems to avoid over exposure. See for example D. B. Plewes, E. Vogelstein, 'A scanning system for chest radiography with regional exposure control: Practical implementation', Medical Physics, volume 10 number 5, 655-663, 1983.

Similarly, computed tomography (CT) systems adjust the exposure at each view to ensure the dynamic range of response of the detector array is used most efficiently, as set out in L. Jangland, E. Helmius, 'Automatic exposure control on CT systems', Radiology, volume 201, 792S, 1996, U. Nyman, T. L. Ahl, M. Kristiansson, L. Nilsson, S. Wettemark, 'Patient-circumference-adapted dose regulation in body computed tomography. A practical and flexible formula', Acta Radiologica, volume 46 number 4, pages 396-406, 2005, and T. H. Mulkens, P. Bellinck, M. Baeyaert, D. Ghysen, X. Van Dijck, E. Mussen, C. Venstermans, J. L. Termote, 'Use of an automatic exposure control mechanism for dose optimization in multi-detector row CT examinations: Clinical evaluation', Radiology, volume 237 number 1, 213-223, 2005.

A chest radiography scanning system has been described by Odelft, whereby the radiation intensity distribution is adapted to ensure optimum exposure at all points. This system is described in H. Vlasbloem, L. J. Schultze Kool, 'AMBER: A Scanning Multiple-Beam Equalization System for Chest Radiography', Radiology, volume 169, 29-34, 1988.

A mammography system has also been proposed, which would use information gained from the leading edge of a scanning beam to modify the scan velocity in M. Åslund, B. Cederström, M. Lundqvist, M. Danielsson, 'AEC for scanning digital mammography based on variation of scan velocity', Medical Physics, volume 32 number 11, 3367-3374, 2005.

SUMMARY OF THE INVENTION

The invention relates to an imaging system that is capable of adapting to the imaging task in a way, that is controlled by diagnostic features within the image. Furthermore, this adaptation is achieved with a single source and in a single pass of the object to be imaged.

Thus, the invention provides a method and arrangement which enables the subject of the x-ray imaging system to be so exposed, as to provide improved diagnostic information. To this end, the image from the radiated item is firstly analyzed in order to assess its diagnostic quality and subsequently the exposure conditions are adapted accordingly in real-time.

The prior systems discussed above all operate well, but they are all designed to adapt the exposure to the patient, so as to ensure that the detector receives an exposure within its operating dynamic range. Thus, although the detector may be optimally exposed the object may not be.

In embodiments, the X-ray beam is split into two fan beams by the use of a collimator. The object to be imaged is scanned by both beams. The beam that the object encounters first is referred to as the 'scout' beam and the second beam will also be referred to as the 'I-ImaS' beam.

In a single pass of the object the diagnostic information is recorded. Unlike existing systems the exposure factors are not pre-selected according to experience, but are adjusted on a point by point basis and thus optimized for all points in the image at the time of exposure.

BRIEF DESCRIPTION OF THE DRAWINGS

In the following, the invention will be further described in a non-limiting way under reference to the accompanying drawings, in which.

DETAILED DESCRIPTION OF THE EMBODIMENTS

Figure 1:
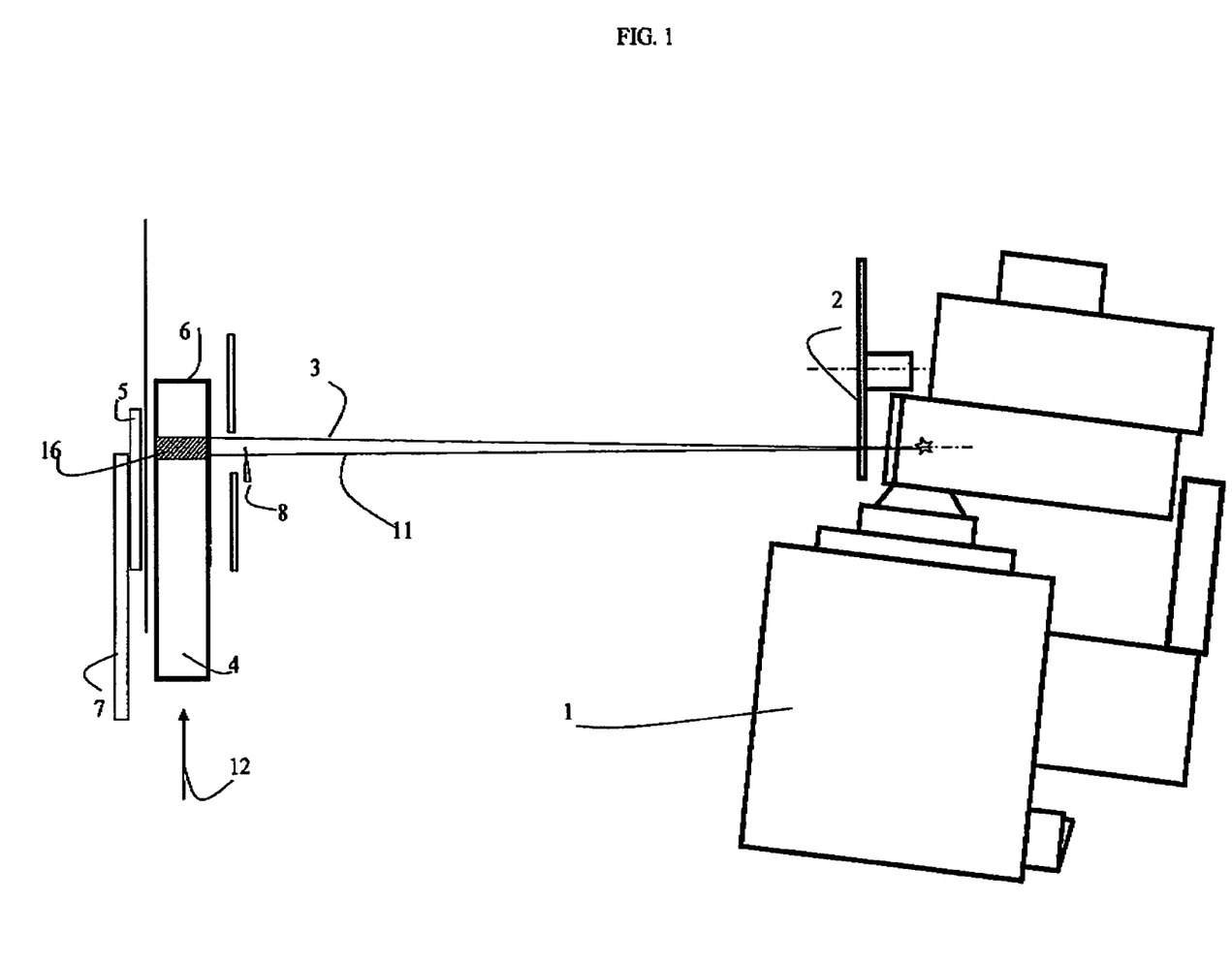
FIG. 1 is a plan view of the intelligent adaptive x-ray imaging system incorporating the scout and I-ImaS radiation beams.
Figure 2:
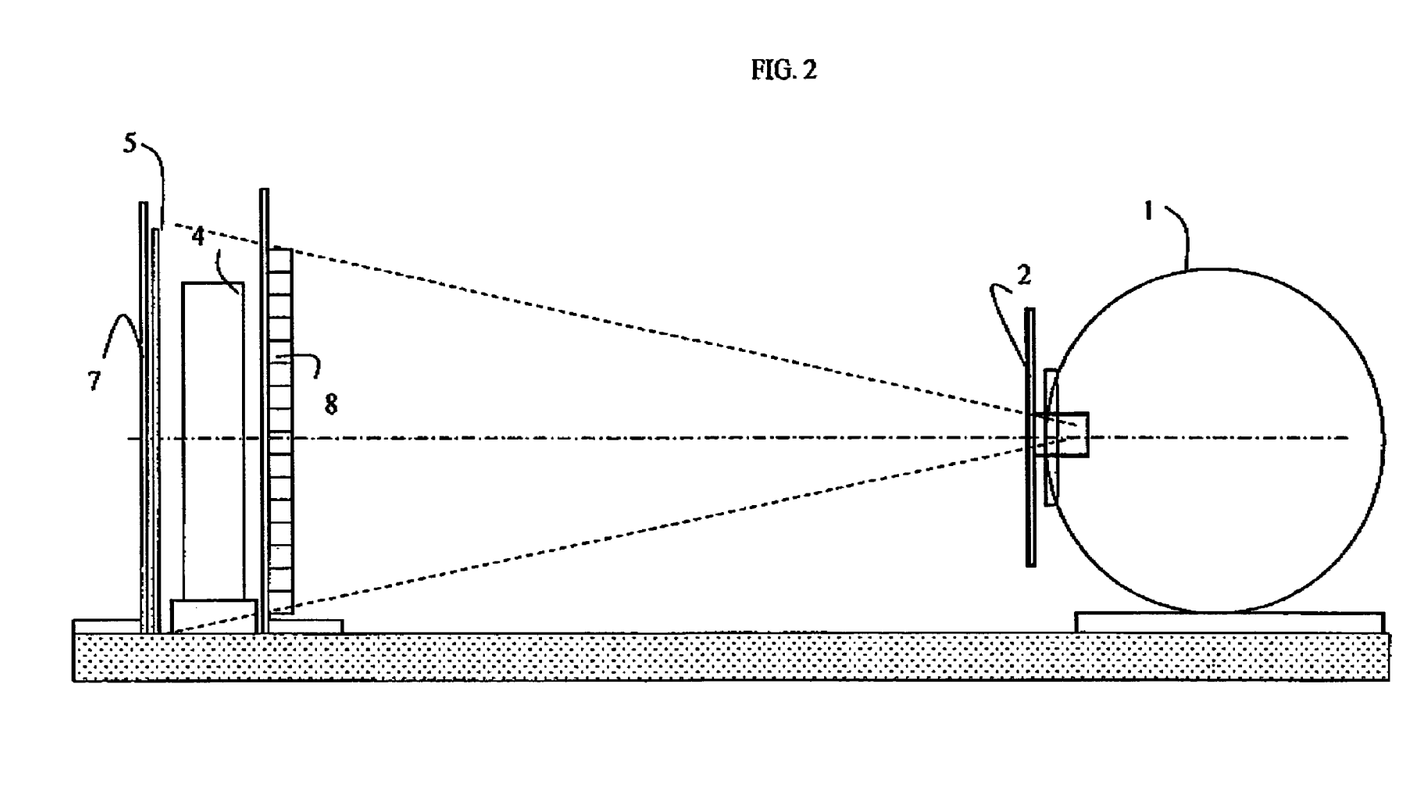
FIG. 2 is a side elevation view of the said system in FIG. 1.

Referring to FIGS. 1 and 2, a source of ionizing radiation 1, in the embodiment X-rays, produces a conical beam, that is divided into two fan beams 3, 11 by the collimator system 2. These beams are labeled scout beam 3 and second beam 11, the latter may also referred to as 'I-ImaS' beam.

These beams 3, 11 and respective sensors 5 arranged to detect each beam are scanned across an object 4 to be imaged 4 such that the second beam follows the scout beam. This may be done by moving the beams, but in the embodiment the object 4 is moved in the direction of arrow 12 (FIG. 1) keeping the collimator 2, beams and sensors 5 fixed.

Figure 5:
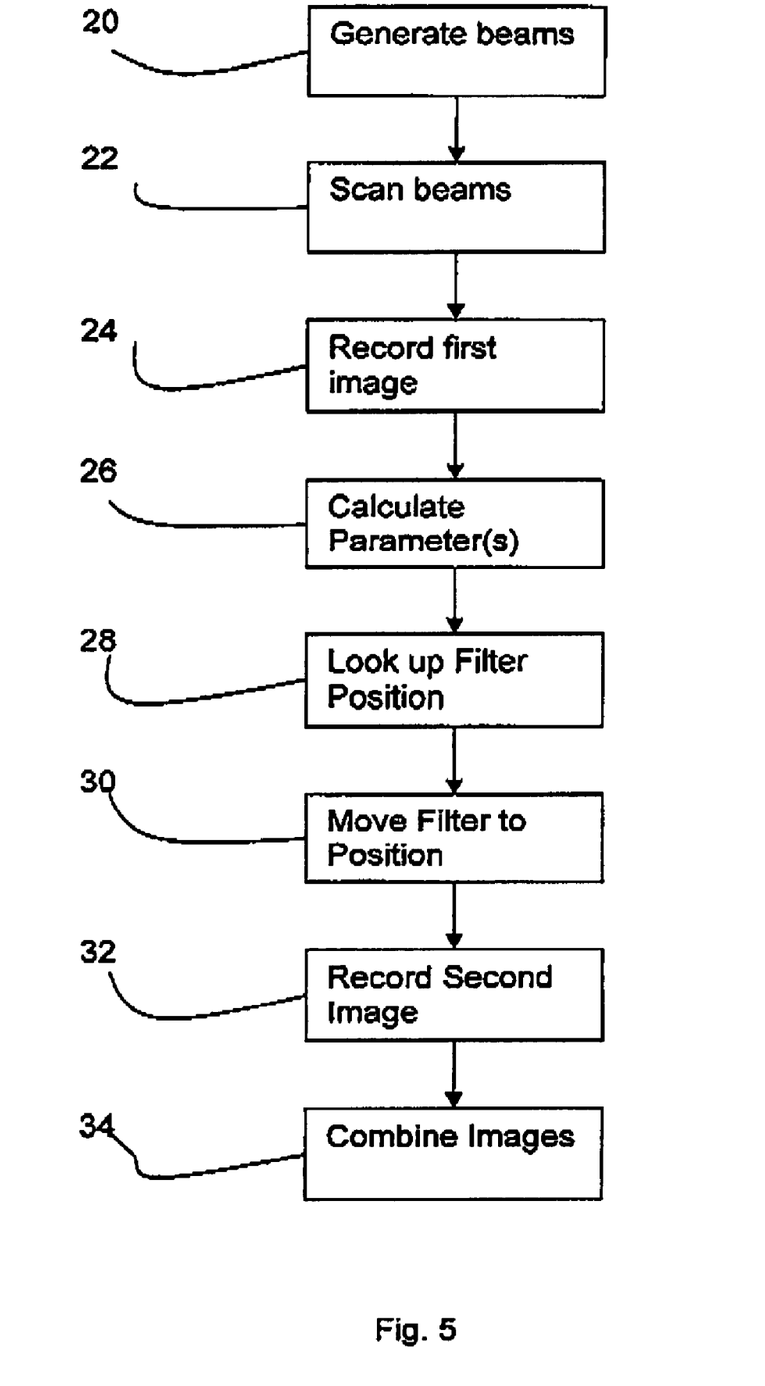
FIG. 5 is a flow chart of the method used.

In a summary of the method, the system carries out the method illustrated in flow chart form in FIG. 5.

The system generates 20 first and second imaging beams and scans 22 the first and second imaging beams over the object with the second beam following the first beam. The system records 24 an image of the object with the first beam over a plurality of regions of interest 16, each region of interest including a plurality of pixels.

Then, for each region of interest, the system calculates 26 at least one parameter, for example standard deviation.

The system then looks up 28 the correct filter position for the parameters, and moves 30 the respective filter to the looked up position. In this position, a second image of the object is recorded 32.

The two images are then combined 34 to make a final image.

By varying the filter position for the second beam, an improved beam intensity, in some sense, can be adopted in real time for the second beam thereby improving the image. For example, the dose used in the second beam can be reduced in areas where there is little information. Alternatively or additionally, the intensity of the second beam can be adjusted.

The x-ray beam intensity after leaving the collimator system 2 is split between the beams 3, 11 equally. This is not however essential and filtration can be placed at the collimator such that the intensity splitting between the two beams could be varied. In the embodiment each beam gets between 40% and 60% of the intensity. Thus, when imaging a gland using an average mean glandular dose that dose may be split roughly equally between the scout beam and the main beam.

The scout beam 3 travels uninterrupted to the object to be imaged 4, it is attenuated as it goes through the object and then it reaches the sensor 5.

The sensors 5 used in this embodiment are CMOS image sensor devices combined with integral data acquisition units 7. CMOS sensors are known, for example from A. El Gamal, H. Eltoukhy, 'CMOS Image Sensors', IEEE Circuits & Devices Magazine, volume 21 number 3, 6-20, May/Jun. 2005; P. Denyer, D. Renshaw, G. Wang, M. Lu, S. Anderson, 'On-chip CMOS sensors for VLSI imaging systems', Proc. VSLI-91, 157-166, 1991 and R. H. Nixon, S. E. Kemeny, B. Pain, C. O. Staller, E. R. Fossum, '256×256 CMOS active pixel sensor camera-on-a-chip', IEEE Journal of Solid-Stage Circuits, volume 31 number 12, 2046-2050, 1996.

The reason for the use of CMOS sensors in this embodiment is that they react quickly. Accordingly, when combined with the integral data acquisition unit 7 they detect the scout beam and allow the associated data acquisition unit 7 to make rapid decisions about the diagnostic quality of the strip of data received. Based upon these decisions, the second beam 11 can be modified by a series of filters 8 when the second beam encounters the same part of the object. This process continues, as the beams 3, 11 (scout and second) scan across the object. The filters, that modify the I-ImaS beam, can modify beam intensity, spectral distribution, spatial distribution or any combination of these features.

Figure 3:
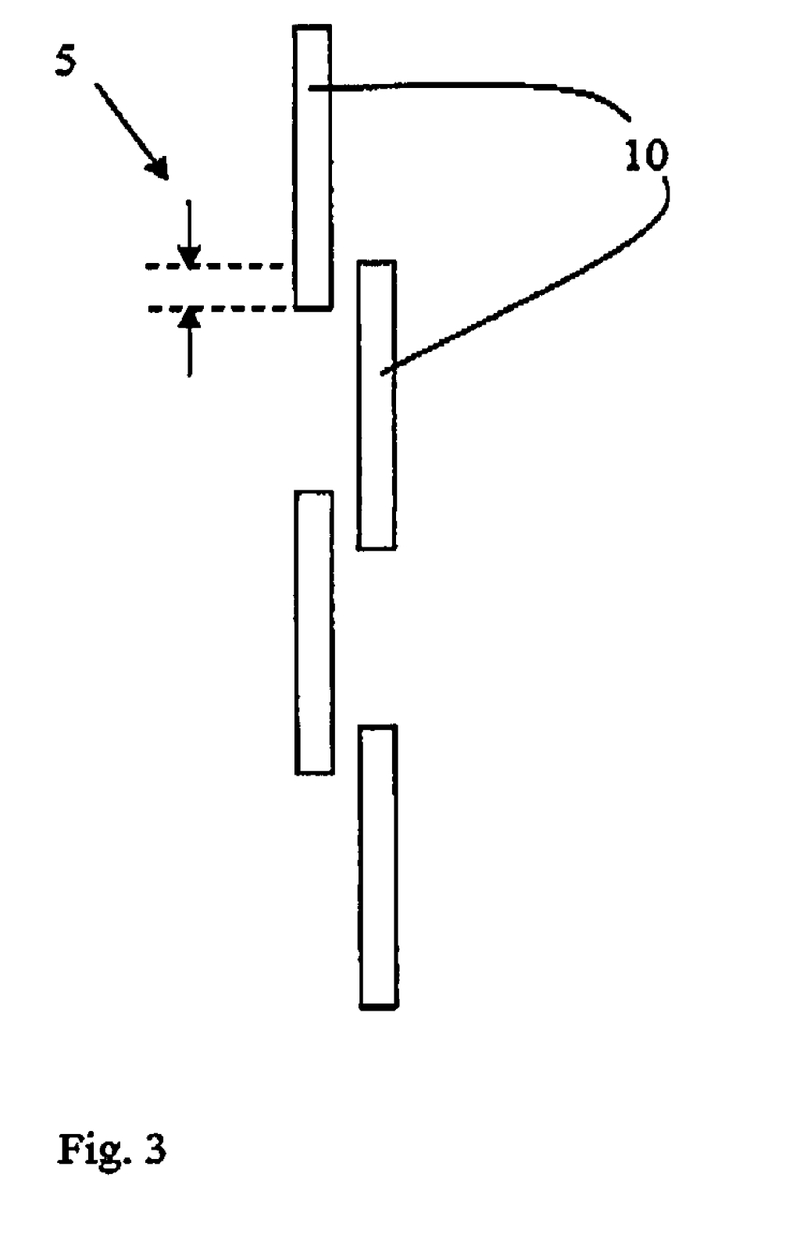
FIG. 3 is a plan of the sensor tiling.

In the embodiment the sensor 5 is formed from an array of tiled smaller sensor elements 14 as one long sensor is very expensive to make. They are tiled in an overlapping arrangement as shown in FIG. 3. The staggering is used as in the embodiment each sensor sits on a small electronics card and so they can not be directly abutted end-on-end to form one continuous length. However, in alternative embodiments either a long sensor or alternative arrays of tiled smaller sensors may be used.

The sensor 5 detects the radiation in a pixel structure as a strip of information about that strip 6 of the object. Each pixel records the radiation incident on it. Within the sensor or within the data acquisition DAQ system 7 attached to the sensor, the data from regions of interest 16 (ROI) are used to compute a diagnostic property of the ROIs.

The ROIs are the regions for which the calculation of the correct filter 8 for the second beam is made. In the embodiment, the ROIs are equal in size to one small sensor element 10 but this is simply for convenience. The ROIs can be any size at all, limited only by the total size of the long sensor. Note that there are a number of ROIs over the whole sample.

A number of parameters are calculated and used to determine the correct filter. An example of such parameters might be the mean and standard deviation of the recorded data from the pixels within the different ROIs. There are many different types of calculation that can be used. The calculations are based on the measured intensity I as a function of x and y over the ROI, which is of size X by Y.

A number of diagnostic parameters of the ROI may be calculated. Particular embodiments may use some or all of the parameters and formulae:

1. Min value $\quad I_{min} = \min\limits_{XY}\{I(x, y)\}$

2. Max value $\quad I_{max} = \max\limits_{XY}\{I(x, y)\}$

3. Mean value $\quad \mu = \dfrac{1}{XY}\sum\limits_{i=1}^{X}\sum\limits_{j=1}^{Y} I(x, y)$ 4. Std. Deviation $\quad \sigma = \sqrt{\dfrac{1}{(XY-1)}\sum\limits_{i=1}^{X}\sum\limits_{j=1}^{Y}(I(x,y)-\mu)^2}$ 5. Skewness $\quad sk = \dfrac{1}{XY}\sum\limits_{i=1}^{X}\sum\limits_{j=1}^{Y}\left(\dfrac{I(x,y)-\mu}{\sigma}\right)^3$ 6. Kurtosis $\quad kr = \left(\dfrac{1}{XY}\sum\limits_{i=1}^{X}\sum\limits_{j=1}^{Y}\left(\dfrac{I(x,y)-\mu}{\sigma}\right)^4\right) - 3$ 7. Signal Power $\quad P_{XY} = \sum\limits_{i=1}^{X}\sum\limits_{j=1}^{Y} \|I(x, y)\|^2$ 8. Entropy $\quad E = \sum\limits_{k=1}^{100} p_{Ghist(k)} \cdot \log(P_{Ghist(k)})$ 9. Zero-Crossings $\quad ZC = \sum \{k : (I_k(x, y) - \mu) \cdot (I_{k+1}(x, y) - \mu) \le 0\}$ 10. Surface $\quad S_{XY} = \sum\limits_{i=1}^{X-1}\sum\limits_{j=1}^{Y-1}(I(x, y) + 1 + \|I(x+1, y) - I(x, y)\| + \|I(x, y+1) - I(x, y)\|)$ 11. Volume $\quad V_{XY} = \sum\limits_{i=1}^{X}\sum\limits_{j=1}^{Y} I(x, y)$ 12. Synth. Feat-12 $\quad SF_{12} = \dfrac{(I_{max} - I_{min})^2}{\mu}$ 13. Synth. Feat-13 $\quad SF_{13} = \dfrac{\mu - I_{min}}{I_{max} - I_{min}}$ 14. Synth. Feat-14 $\quad SF_{14} = \dfrac{\mu}{\sigma}$ 15. Synth. Feat-15 $\quad SF_{15} = \dfrac{P_{XY}}{\mu^2}$ 16. Synth. Feat-16 $\quad SF_{16} = \dfrac{\sqrt{S_{XY}}}{\sqrt[3]{V_{XY}}}$ 17. Synth. Feat-17 $\quad SF_{17} = \dfrac{S_{XY}}{XY}$ 18. Synth. Feat-18 $\quad SF_{18} = \dfrac{ZC}{XY}$ 19. Synth. Feat-19 $\quad SF_{19} = \dfrac{P_{XY}}{XY}$ 20. Synth. Feat-20 $\quad SF_{20} = \log\left(1 - \dfrac{SF_{19}}{255^2}\right)$ A variety of such parameters may be used. The embodiment adopted by the inventors uses the mean (function 3), standard deviation (function 4) and nth percentiles over the region of interest. These have been chosen as they appear to be simple calculations that will give the required results for the system. However, other parameters may also be used, including any of the parameters indicated above, limited only by the processing power available.

The results of the calculations are applied, according to a previously determined steering algorithm, to move the filters 8 into appropriate positions, so that when the second beam 11 reaches the strip 6 of the object, the second beam will be accordingly modified. An appropriate modification can be to reduce the beam intensity by a very large factor, if the corresponding ROI is of little diagnostic value. On the other hand, if the ROI is of high diagnostic use, the filters 8 are moved, so that the strip receives the optimum exposure from the second beam 11.

In general terms, when the calculated value or values of parameters indicate that a ROI is of interest, the filters are used to provide a more intense second beam. When the calculated value or values indicate that an ROI is unlikely to be of interest, the filters are used to reduce the intensity of the second beam. In this way, the dose, which must of course be kept within strict limits, is used to preferentially to measure those ROIs which contain more information and less for those ROIs which contain less. Accordingly, the embodiment delivers improved images for a given dose, or alternatively a lower dose for a given image quality.

The features of an ROI which indicate it is of interest vary depending on what is being imaged, for example breast tissue or dental images. In general terms an ROI of interest is one that has information in it, that is to say it doesn't just show a regular background. This means that in general ROIs are of interest if they show one or more features showing above the usual background of an image.

For example, in a mammographic image, the aim is to find features indicative of cancer (or non-normal areas of the breast). A radiologist would described these as: calcifications (small clusters of tiny dense specks on the image), masses (increased densities on the image), or perhaps distortion of structures within the breast.

In fact, any of a large number of parameters could be used, only some of which are specified above. However the system of the embodiments uses a real-time on-line approach. Thus the time between the scout beam imaging a strip of tissue and the second beam reaching that strip, along with the amount of computing power available, is the key limiting factor in the amount of processing that can be carried out by the system.

This is the reason that the parameters used in the embodiment are the standard deviation and we also use the value of an nth percentile, in an example the 95 percentile, i.e. the measured intensity value for which 95% of pixels have a lower measured intensity value and 5% a higher intensity value. A high standard deviation indicates increasing information in the ROI, and so it is one of interest. A lower standard deviation indicates a more uniform background ROI and thus the beam will be attenuated.

Of course, it is not required that the most interesting ROIs have the highest x-ray beam intensity; instead they should have the optimum beam intensity which may vary depending on the opacity of the ROI.

All these calculations are done on-line within the imaging system data acquisition units 7. These are currently implemented as field programmable gate arrays (FPGAs), but the invention can work with any implementation, for example CMOS devices. The steering algorithm (also within the system) is the bit of software that tells the wedge filters (to be described later) what position they should be in—i.e. whether to increase the intensity of the second beam on the object, or to decrease it, or to keep it the same. Each ROI has an individual filter associated with it, so in this particular case with an ROI being a small sensor element, a filter is positioned in front of each small sensor element, thus attenuating the portion of the second beam incident on that small sensor.

The basis of the steering algorithm is that it is a look up array with a dimension for each of the calculated parameters. The algorithm takes the parameters and then looks up the element in the array that they point to. This element's value then indicates the correct position of the wedge filter for these parameters. In an example using only the standard deviation, a one-dimensional array will specify a filter position for each of a plurality of possible ranges of standard deviation.

In an alternative example using two parameters, the standard deviation and average intensity, the array will be a two-dimensional array. For low standard deviations, the second beam will be strongly attenuated regardless of the average intensity. For high standard deviations, the second beam will be attenuated by a variable amount depending on the average intensity, where a higher beam intensity will be used for relatively opaque regions of the object being measured than for relatively transparent regions to improve the detector sensitivity.

In the example discussed above using two parameters, the standard deviation and the value of the 95th percentile, the array will be a two-dimensional array. For low standard deviations, the second beam will be strongly attenuated regardless of the average intensity. For high standard deviations, the second beam will be attenuated by a variable amount depending on the 95th intensity percentile to ensure that the value of the intensity at the 95th percentile is appropriately positioned at 90% to 100% of the maximum intensity measured by the sensor.

Thus, the system can autorange for best sensitivity in regions of interest and use a low dose in regions of less interest.

In a variation of any of these examples, the relative standard deviation, i.e. the standard deviation divided by the mean, may be used.

Figure 4:
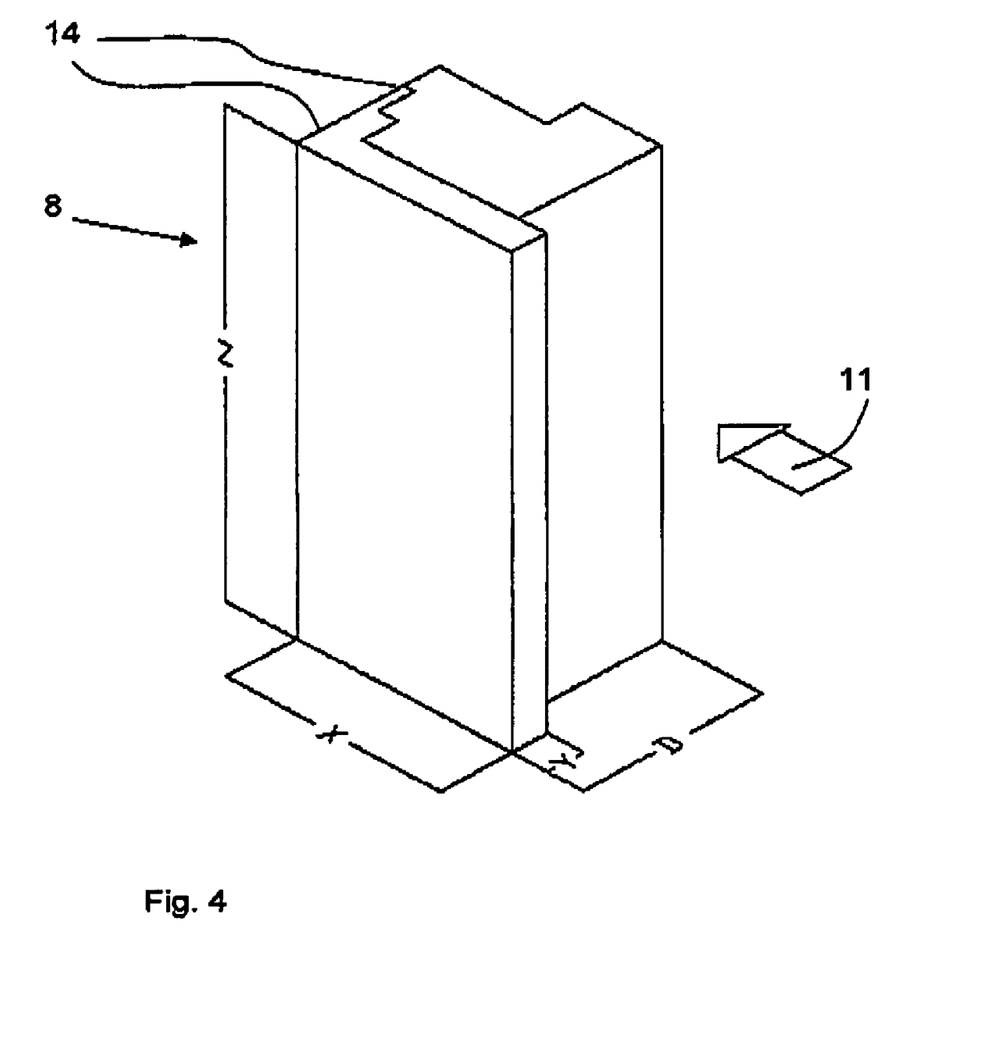
FIG. 4 is a view of the shape of the individual filters.

It will be appreciated by those skilled in the art that the calculations can be done in software or hardware, and that FIG. 4. shows the basic structure of the filters 8. The filter is made up of a step wedge, with a number of steps 14 such that the intensity of an x-ray beam passing through a filter is attenuated so that it falls by either 0%, 20%, 40%, 60%, 80% or 100% nominally. The steps are made of aluminum and Polymethyl methacrylate (PMMA) with the high attenuation steps having a high thickness of aluminum. The thickness is measured in the direction of the second beam 11 indicated with an arrow in FIG. 4. The wedges used in the embodiment have these six steps (the 100% intensity being achieved by moving the filter out of the beam), however the number of steps could be increased to perhaps 10, or decreased, even as far as 2, so the I-ImaS beam would be either 'on' or 'off'. The y and z dimensions are set such that a single step of the filter is capable of attenuating the x-rays incident on a single ROI.

The filters modify the intensity of the beam. In embodiments, the filters also modify the beam spectrum where a polyenergetic x-ray beam is used.

The filter dimensions are tailored for a specific incident x-ray spectrum (i.e., a 40 kVp Mo/Mo x-ray source requires different filtration to a 70 kVp W/Al beam in order to achieve the same nominal values of attenuation). A set of different filters may accordingly be provided, for example three sets of filters: 40 kVp Mo/Mo, 40 kVp W/Al, 80 kVp W/Al.

After the imaging process, data from both the scout beam scan and the second beam scan is combined to form the final image.

The invention is not limited to the shown embodiments and can be varied without departing from the scope of the appended claims and the arrangement and the method can be implemented in various ways depending on application, needs and requirements.

Industrial applications of this invention are identified in the areas of digital mammography, encephalography, other healthcare imaging, industrial inspection and security, such as baggage scanning.

We claim:

1. A method of X-ray imaging an object, comprising
generating first and second imaging beams;
scanning the first and second imaging beams over the object with the second beam following the first beam;
recording an image of the object with the first beam over a plurality of regions of interest, each region of interest including a plurality of pixels;
calculating at least one parameter for each of the regions of interest;
varying the second beam for each of the regions of interest based on the respective calculated parameters;
recording an image of the object with the second beam over the plurality of regions of interest; and
combining the images recorded by the first and second beams, wherein:
the first beam is a fan beam extending in a first beam direction;
the second beam is a fan beam extending in a second beam direction; and
the first and second beam directions are substantially perpendicular to each other.

2. A method according to claim 1, wherein the step of varying the second beam comprises moving a filter to vary a beam intensity of the second beam for each of the respective regions of interest.

3. A method according to claim 1, wherein the step of varying the second beam comprises moving a filter to vary a beam spectrum for the second beam for each of the respective regions of interest.

4. A method according to claim 1, wherein the step of varying the second beam comprises looking up a filter position in a look up table based on the respective calculated parameters and moving the filter to the filter position indicated in the look up table.

5. A method according to claim 4, wherein the parameters include the standard deviation of a beam intensity in the region of interest and the look up table defines fitter positions such that standard deviation parameter values above a predetermined value have lower attenuations of the second beam than standard deviation parameter values below a predetermined value.

6. X-ray imaging apparatus, comprising:
an X-ray source for generating X-rays;
a collimator for generating first and second imaging beams;
a means for scanning the first and second imaging beams relative to object with the second beam following the first beam;
a sensor for recording an image of the object over a plurality of regions of interest using the first beam, each region of interest including a plurality of pixels;
a processor for calculating at least one parameter for each of the regions of interest;
a variable filter for varying the second beam for each of the regions of interest based on the respective calculated parameters; and
a further sensor for recording an image of the object over a plurality of regions of interest using the second beam,
wherein the processor comprises a look up table defining for a plurality of calculated parameters a respective plurality of filter positions, and the look up table defines filter positions such that standard deviation parameter values above a predetermined value have lower attenuations of the second beam than standard deviation parameter values below a predetermined value.

7. X-ray imaging apparatus according to claim 6, wherein the variable filter has a plurality of different attenuation values.

8. X-ray imaging methods, where the radiation is controlled in such a manner as to optimize exposure, characterized in that an imaging beam is split into two separate fan beams that scan over an object, where one beam collects information that is analyzed to control intensity or spectral quality or spatial distribution of the second beam and the combination of signals from both beams are added together, so that diagnostic information is optimized.

9. X-ray imaging methods according to claim 8, characterized in that a scout beam sensor, that receives information, can process detected information either on-chip or within a Field Programmable Gate Array (FPGA), so as to compute a measure related to a diagnostic value of the information.

10. X-ray imaging methods according to claim 8 or 9, characterized in that one or more beams from a radiation source can be intensity modulated according to the diagnostic information collected from at least one other beam.

11. X-ray imaging methods according to claim 8, characterized in that one or more beams from a radiation source can be spectral quality modulated according to the diagnostic information collected from at least one other beam.

12. X-ray imaging methods according to claim 8, characterized in that one or more beams from a radiation source can be spatially modulated according to the diagnostic information collected from at least one other beam.

* * * * *

UNITED STATES PATENT AND TRADEMARK OFFICE
CERTIFICATE OF CORRECTION

PATENT NO.         : 7,664,227 B2                                              Page 1 of 1
APPLICATION NO.    : 11/801782
DATED              : February 16, 2010
INVENTOR(S)        : Speller et al.

It is certified that error appears in the above-identified patent and that said Letters Patent is hereby corrected as shown below:

Column 7, Claim 6, line 48, after "relative to" insert -- an --

Signed and Sealed this

Thirteenth Day of July, 2010

David J. Kappos
*Director of the United States Patent and Trademark Office*